United States Patent [19]

Razete

[11] 4,089,655

[45] May 16, 1978

[54] AIR PURIFICATION SYSTEM

[75] Inventor: John J. Razete, Cincinnati, Ohio

[73] Assignee: Aero-Dri Corporation, Cincinnati, Ohio

[21] Appl. No.: 734,092

[22] Filed: Oct. 20, 1976

Related U.S. Application Data

[63] Continuation of Ser. No. 657,569, Feb. 12, 1976, abandoned, which is a continuation of Ser. No. 389,575, Aug. 20, 1973, abandoned.

[51] Int. Cl.² ............................ B01J 8/02; B01J 8/04; A61L 9/06

[52] U.S. Cl. ................................ 23/288 F; 23/288 R; 23/288 FB; 21/74 R; 55/DIG. 17

[58] Field of Search ............ 21/74 R; 23/288 F, 284, 23/288 R, 288 FB; 55/DIG. 17; 211/13, 71, 74; 248/129

[56] References Cited

U.S. PATENT DOCUMENTS

| | | | |
|---|---|---|---|
| 1,422,211 | 7/1922 | Lamb | 23/288 FB UX |
| 1,736,839 | 11/1929 | Schiller et al. | 21/74 R |
| 2,760,647 | 8/1956 | Saul, Jr. | 280/79.3 UX |
| 3,219,414 | 11/1965 | Berry | 423/262 |
| 3,280,988 | 10/1966 | Bennett | 211/71 |
| 3,306,711 | 2/1967 | Angerhofer | 23/288 R X |
| 3,341,219 | 9/1967 | Marini et al. | 211/71 X |
| 3,476,524 | 11/1969 | Burke | 23/288 FB |
| 3,587,210 | 6/1971 | Shriner | 23/288 FB X |
| 3,672,824 | 6/1972 | Tamura et al. | 423/247 |
| 3,705,480 | 12/1972 | Wireman | 55/DIG. 17 UX |

OTHER PUBLICATIONS

Pall Trinity Micro Corp.-Type A Heat-Reactivated Desiccant Dryers = Bulletin, A-3090, 7/14/67.

Sargent-Welch Scientific Co., p. 1018 - Catalogue 119, © 1971.

*Primary Examiner*—Morris O. Wolk

*Assistant Examiner*—Michael S. Marcus

*Attorney, Agent, or Firm*—John G. Schenk

[57] ABSTRACT

An air purification system accepts foul air from a source of high pressure and treats the air so as to deliver an acceptable breathable air usable in any life support package. The components of the system are mounted on a portable cart. The foul air passes through a plurality of stages in going from the foul to the usable condition. The air is monitored at the various positions along the system to insure that the system is operational.

8 Claims, 5 Drawing Figures

AIR PURIFICATION SYSTEM

This application is a continuation of application Ser. No. 657,569, filed Feb. 12, 1976 which was a continuation of application Ser. No. 398,575, filed Aug. 20, 1973, each abandoned.

BACKGROUND OF THE INVENTION

This invention relates generally to purifiers and more particularly to an air purification system for producing usable breathable air which may be used in life support packages.

There are many uses for life support packages which include tanks of usable and breathable air. Examples of such uses would be a package carried on aircraft, military or commercial, for use in emergency situations; use by firefighters in smoke filled areas; personnel working within containers or areas not having breathable air therein; underwater recreational use, such as scuba divers; etc. Breathable air must be provided at a high pressure to charge the air tanks. Air compressors will provide a high pressure source of air, but this air is most generally not acceptable for use in air tanks due to the contamination of the air. Accordingly, it is an object of this invention to provide an air purification system which will accept a high pressure foul air and treat the air so as to provide a breathable usable air, said air being delivered at a sufficiently high pressure to charge air tanks.

Another object of this invention is to provide an inexpensive air purification system which can be connected with any air compressor to provide breathable air.

Yet another object of this invention is to provide a self-contained, portable air purification system having a multiplicity of standard parts.

And still another object of this invention is to provide an air purification system having a means to continuously monitor the air passing therethrough.

SUMMARY OF THE INVENTION

This invention provides an improved air purification system for treating foul air to provide a breathable usable air which may be used to charge air tanks for use in life support packages. The system processes air in stages to remove moisture, remove gaseous hydrocarbons, convert carbon monoxide (CO) to carbon dioxide ($CO_2$) and to sweeten the air. The components of the air purification system are mounted on a portable structure for ease in maneuverability and positioning. The air passes through a plurality of containers in which the above mentioned processing stages take place. Means for monitoring the air in the system is provided.

Other objects, details, uses and advantages of this invention will become apparent as the following description of the exemplary embodiment thereof presented in the accompanying drawings proceeds.

BRIEF DESCRIPTION OF THE DRAWINGS

The accompanying drawings show a present exemplary embodiment of this invention in which.

DESCRIPTION OF ILLUSTRATED EMBODIMENT

In the performance of this invention, a high pressure source of contaminated or foul air is processed in stages to produce a breathable usable air supply. An example of such a high pressure source of air is any commercially available air compressor which provides air in the 4500 psi range. Air from the compressor is transmitted to the first stage wherein the air passes through a suitable media to remove the moisture level of the air to approximately −70° F. dew point. Suitable media would be a molecular sieve type 4A manufactured by Linde Division of Union Carbide or a silica gel (6–12 mesh) produced by Eagle Chemical located in Mobile, Alabama.

It has been found that compressor air often includes gaseous hydrocarbons due to the seepage of such hydrocarbons past seals in the compressor unit itself. Accordingly, the air from the first stage is then transmitted to a second stage wherein the air is passed through a suitable media which will pick up any oil being carried thereby and will remove gaseous hydrocarbons to a level of no more than 1.3. An example of a suitable media for the second stage is a molecular sieve type 13X also obtainable from Linde Division of Union Carbide.

The atmosphere has an acceptable amount of CO present which is not harmful to humans. However, a compressor engine generates CO and any atmospheric turbulence around the compressor may cause an excessive amount of CO to be drawn into the air system which could result in a CO level which would be harmful to humans. Hence, air from the second stage is transmitted to a third stage for passage through a catalyst material which converts CO to $CO_2$. A suitable catalyst material is Hopocolite obtainable from Mine Safety Appliances.

The air from stage 3 is then passed to a final stage for sweetening. Compressor air may have a foul odor due to the cracking of hydrocarbons, fuel of the compressor and gas odors seeping past seals, and such odors are generally unacceptable for use by persons in breathable air of the life support package. The final stage consists of passing the air through a suitable media such as activated charcoal which will remove the foul odors and make the air sweet and acceptable for use. The air from the final stage is transmitted to a suitable life support package such as an air container or the like.

Figure 1:
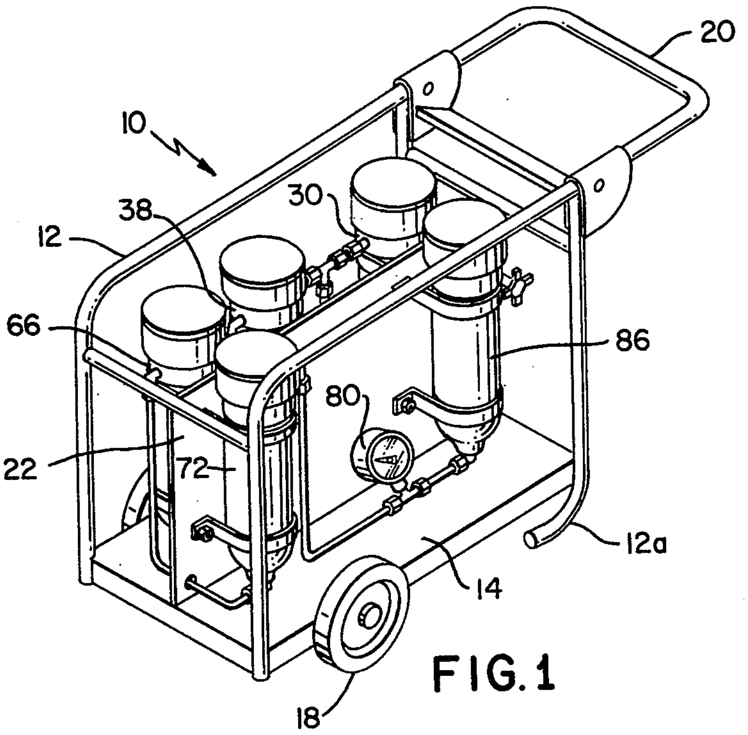
FIG. 1 is a perspective view illustrating an exemplary embodiment of the components of the air purification system mounted on a portable framework structure.

Reference is now made to FIG. 1 of the drawings, which illustrates one exemplary embodiment of an air purification system apparatus to accomplish the process hereinabove described, which is designated generally by the reference numeral 10. The apparatus 10 is comprised of a tubular framework 12 securedly mounted on a base 14. The frame and base may be formed of any suitable strength material such as steel or the like. The base 14 is provided with a pair of sides 14*a* and 14*b* (FIGS. 2 and 3) through which an axle 16 is mounted. Wheels 18 are mounted on the axle 16 so that the apparatus 10 may be easily moved from one position to another. A portion 12*a* of the frame 12 extends below the base 14 to act as a support at that end. A handle 20 is spring loaded by a suitable spring member so that the handle will be held in either the up or down positions. A supporting structure such as a center plate 22 is securedly fixed to the base 14. The plate 22 is of sufficient rigidity and strength to support the components to be described hereinbelow. The components to be hereinbelow described are mounted by suitable brackets and the like to the center plate 22 and supported thereby.

Figure 2:
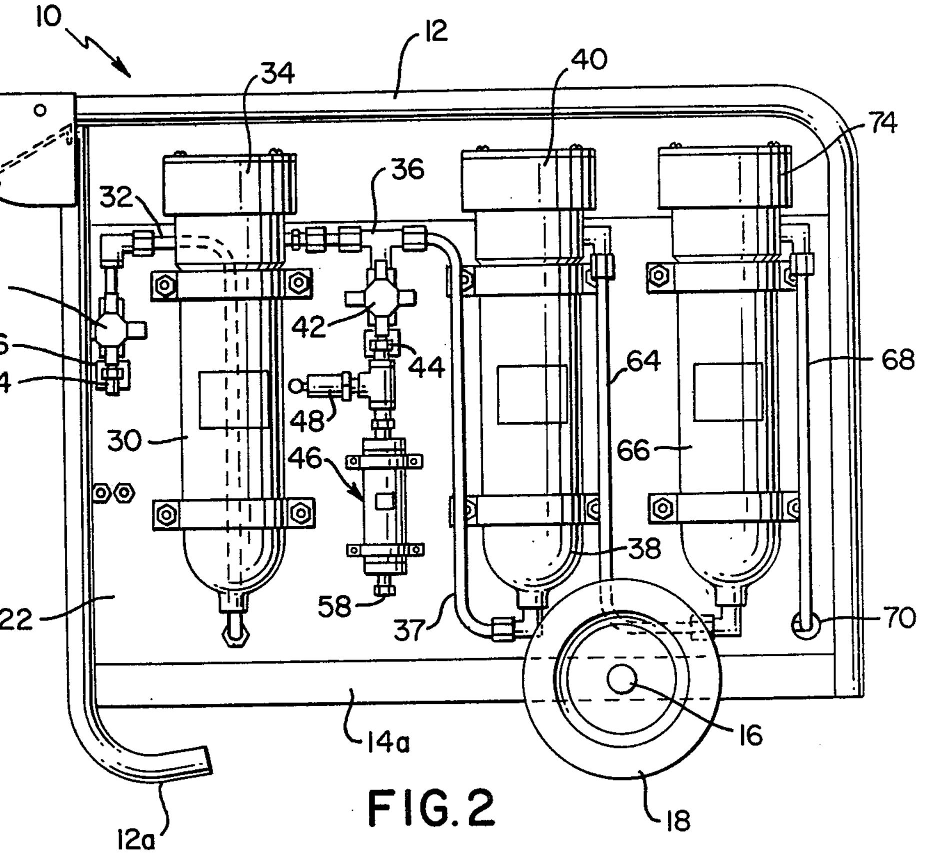

Referring now to FIG. 2, a hose fitting 24 is secured to a mounting bracket 26 which in turn is mounted on the center plate 22. The hose fitting 24 is adapted to receive the outlet hose from the air compressor (not shown). A high pressure needle valve 28 is connected with the fitting 24 and upstream of the cylindrical housing 30. The valve 28 may be manually opened and closed to permit or stop flow from the compressor to the first stage defined by the cylinder 30. Valve 28 is connected by suitable tubing 32, such as stainless steel, to the lower end of cylinder 30. The cylinder 30 is secured by suitable mounting brackets to the center plate 22.

The cylinder 30 is provided with a removable cap and rain cover designated generally as 34. The molecular sieve hereinabove mentioned is placed within the cylinder housing 30 such that moisture in the air passing therethrough is removed. As hereinabove described, air leaving the first stage or cylinder 30 has an approximate dew point of −70° F.

The outlet of cylinder 30 is connected with a branch tee fitting 36. It should be noted that suitable connectors and tubing are provided in the airline and such individual connectors and tubing sections will not be individually described. One outlet of the tee 36 is connected via tube 37 with the inlet of the second stage defined by cylinder 38. Carried within the cylinder 38 is the molecular sieve to remove the gaseous hydrocarbons in the second stage. The cylinder 38 is similarly provided with a removable cap 40 through which the sieve may be replaced. Cylinder 38 is secured to the center plate 22 by suitable mounting brackets.

A valve 42 is connected with the second outlet of the branch tee 36. Valve 42 is connected with a flow limiter 44 which limits the pressure buildup within a dew point indicator, designated generally as 46, to 300 psi. A safety valve 48 is connected between the flow limiter 44 and dew point indicator 46.

Figure 5:
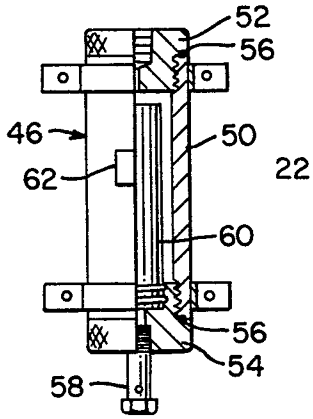
FIG. 5 is an enlarged elevational view, partially in cross-section, of the dew point indicator.

Referring now to FIG. 5, it is seen that the dew point indicator 46 is comprised of a body 50 of a transparent material such as plexiglass or the like. The body 50 is closed by threadable end caps 52 and 54. Suitable O-rings 56 provide airtight seals in the indicator 46. The cap 52 is provided with an inlet connectable with suitable tubing to receive air therethrough. A bleed valve 58 is connected with the end cap 54 to permit the bleeding of air therefrom. A cartridge 60 of a suitable dessicant material is mounted within the indicator 46. A color chart 62 provides a visual indication of the efficiency of the dehydration process occurring in the first stage. By comparing the color of the cartridge 60 with the color chart 62, it is possible to determine when the cartridge in the cylinder 30, i.e., the first stage molecular sieve, is spent and the air coming from the first stage is above the desired −70° F. dew point.

When the valve 42 is opened air is bled from the tee 36 through the limiter 44 to the dew point indicator 46. If a malfunction should occur such that the air cannot be bled off through the valve 58, the safety valve 48 will open when a predetermined pressure is reached to permit escape of the air therethrough. This will prevent damage to the indicator 46.

Figure 3:
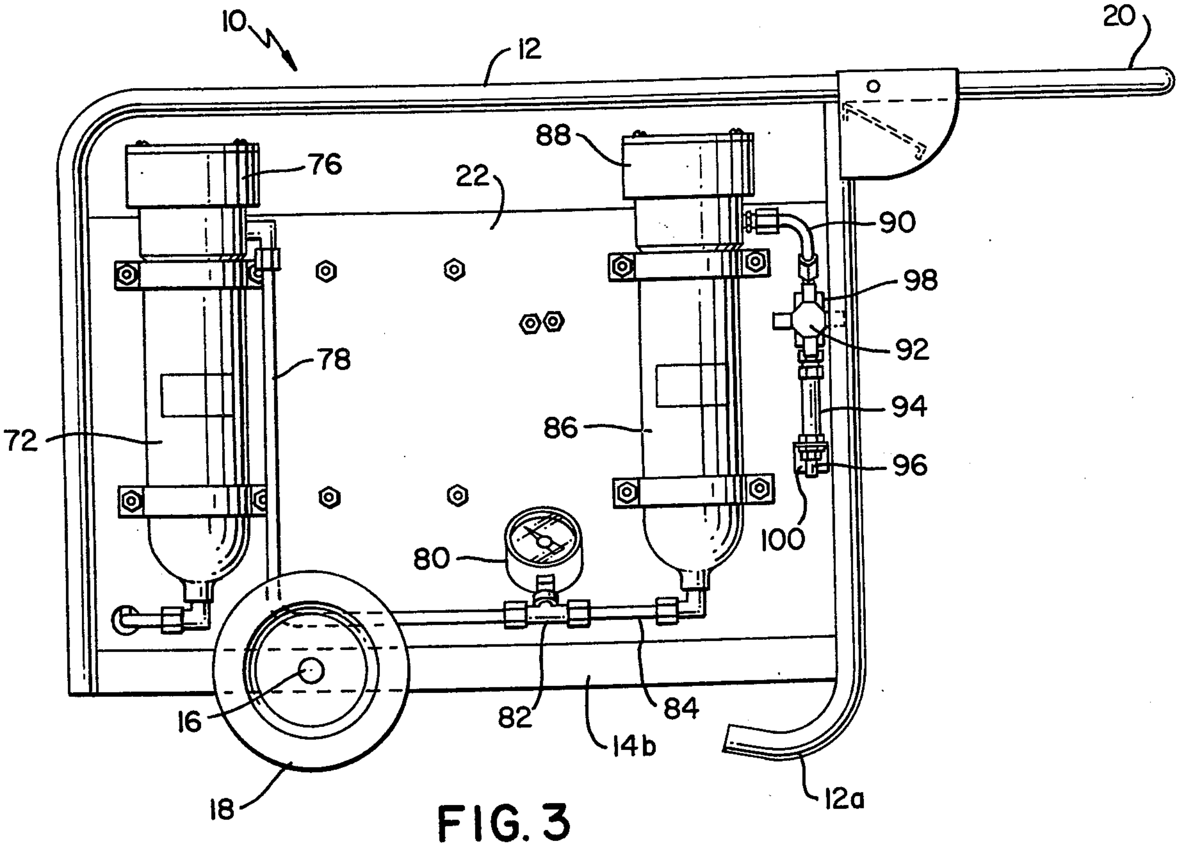
FIGS. 2 and 3 are elevational view of the components of the air purification system mounted in the framework structure.
Figure 4:
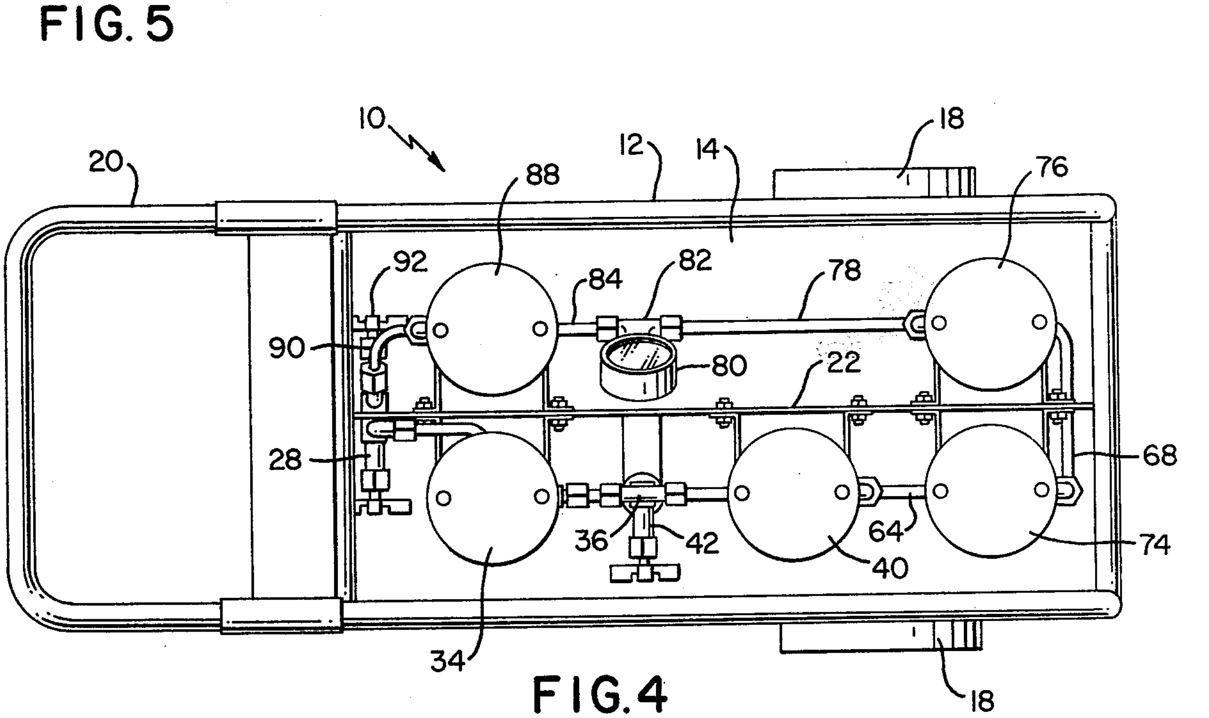
FIG. 4 is a top view of the structure of FIG. 1.

The air from the second stage or cylinder 38 is transmitted via tube 64 to the inlet end of the third stage. The third stage is defined by a pair of cylinders 66 and 72, as seen in FIGS. 2, 3 and 4. Cylinders 66 and 72 are mounted on opposite sides of the center wall 22 and are connected by tube 68 which passes through an aperture 70 in the wall 22. The cylinders 66 and 72 are respectively filled with the Hopocolite material which converts any CO in the air into $CO_2$. The Hopocolite is inserted into the respective cylinders by removing the covers 74 and 76 respectively. The conversion of CO into $CO_2$ will only occur when there is a dry air present. For this reason, it is necessary that the air pass through the first stage which reduces the moisture content in the air to a −70° F. dew point. In the present embodiment, a pair of cylinders is used in the third stage for safety reasons. It should be realized that a single cylinder of larger dimension may be used to obtain the same results.

The air from the outlet of cylinder 72 is transmitted via tube 78, tee 82 and tube 84 to the inlet of the fourth stage defined by the cylinder 86. A high pressure gauge 80 is connected with the tee 82 to measure the pressure within the system. Any suitable gauge measuring pressure from 0 to 5000 psi may be used. The gauge 80 provides a visual indication of the pressure buildup within the flow system.

The fourth stage, defined by the cylinder 86 and removable cover 88, includes an activated charcoal cartridge carried within the cylinder 86. Air passing therethrough has the odors removed and is thereby considered sweetened.

Air is transmitted from the outlet of the cylinder 86 via tube 90 to a high pressure valve 92. The outlet of valve 92 is connected with a priority valve 94, such as a ball check valve. The valve 94 will not open until pressure therein has reached 2400 psi. At this point, the valve will open slowly until full open is reached, thereby permitting an air tank (not shown) to be connected with the hose fitting 96. Valves 92 and 94 are mounted by suitable brackets 98 and 100 to the center wall 22. The valve 92 is a manually operable valve which permits an operator to shut off the system. When the pressure within the system has reached a desirable level, as indicated on the gauge 80, the valve 92 may be opened to permit the filling of an air tank or the like.

It can be seen that this invention provides a self-contained portable air purification system which transforms foul air from a source such as an air compressor into breathable usable air. The air is acted upon in four stages, each of which is defined by uniform cylinders.

While a present exemplary embodiment of this invention has been illustrated and described, it will be recognized that this invention may be otherwise variously embodied and practiced by those skilled in the art.

What is claimed is:

1. An apparatus for purifying contaminated air from a high pressure source such as a compressor or the like for delivery to a tank or the like as breathable air for breathing or the like by a human being comprising carrier support means; a first stage container securedly mounted on said carrier support means; said first stage container having an inlet and an outlet; said inlet of said first stage container receiving the contaminated air from the high pressure source; dehydrating means disposed within said first stage container to remove moisture from the air passing through said first stage container so that the moisture level of the air is at a predetermined dew point when passing through said outlet of said first stage container; a second stage container securedly mounted on said carrier support means; said second stage container having an inlet and an outlet; first means connecting said outlet of said first stage container and said inlet of said second stage container; bleed means connected to said first connecting means to bleed off a portion of the air passing through said first connecting means, said bleed means including a shut-off valve connected to said first connecting means, a flow limiter connected to said shut-off valve, indicating means to provide an indication of the moisture level of the air passing through said first connecting means and connected to said flow limiter, said flow limiter limiting the pressure in said indicating means, a safety valve connected between said flow limiter and said indicating means to prevent excessive pressure build up in said indicating means, and a bleed valve connected with said indicating means to permit bleed off of air therein; means disposed within said second stage container to remove hydrocarbons from the air passing through said second stage container; third stage container means securedly mounted on said carrier support means; said third stage container means having an inlet and an outlet; second means connecting said inlet of said third stage container means with said outlet of said second stage container; said third stage container means including at least one container; catalyst material means disposed within said third stage container means to convert carbon monoxide in the air passing through said third stage container means to carbon dioxide; a fourth stage container securedly mounted on said carrier support means; said fourth stage container having an inlet and an outlet; means disposed within said fourth stage container to remove odors from the air passing through said fourth stage container; third means connecting said outlet of said third stage container means with said inlet of said fourth stage container; and fourth means connecting said outlet of said fourth stage container with the tank or the like to which the purified air is supplied to charge the tank.

2. The apparatus according to claim 1 in which said third stage container means includes a pair of container, each of said pair of containers having an inlet and an outlet, each of said pair of containers having catalyst material means disposed therein so that the air flowing from said inlet to said outlet passes therethrough, means connecting said outlet of the first one of said pair of containers with said inlet of the second one of said pair of containers, said second connecting means connecting said inlet of the first one of said pair of containers with said outlet of said second stage container, and said third connecting means connecting said outlet of the second one of said pair of containers with said inlet of said fourth stage container.

3. The apparatus according to claim 1 including gauge means disposed in said third connecting means to indicate the pressure of the air in said third connecting means.

4. The apparatus according to claim 3 including a line connecting said inlet of said first stage container with the high pressure source, a first shut-off valve disposed in said line to allow flow of air from the high pressure source to said inlet of said first stage container when open and to stop flow of air from the high pressure source to said inlet of said first stage container when closed, and a second shut-off valve disposed in said fourth connecting means to allow flow of air from said fourth stage container when open and to stop flow of air from said fourth stage container when closed.

5. The apparatus according to claim 4 including pressure responsive means in said fourth connecting means downstream of said second shut-off valve to allow flow through said fourth connecting means to the tank only when the pressure exceeds a predetermined pressure and said second shut-off valve is open.

6. The apparatus according to claim 1 in which said carrier support means includes a base and a center plate secured to said base and extending upwardly therefrom; each of said containers is mounted on said center plate; and at least two of said containers are mounted on each side of said center plate.

7. The apparatus according to claim 6 in which said carrier support means includes a pair of wheels rotatably secured to said base adjacent one end thereof, a framework securedly mounted to said base, a portion of said framework extending below said base at the other end thereof to provide a support for said base, and a handle pivotally secured to said framework to permit moving of said carrier support means from one location to another.

8. The apparatus according to claim 7 in which each of said containers has its inlet at its bottom and its outlet adjacent its top, and each of said containers has a removable top to enable removal of said means disposed therein when necessary.

* * * * *